United States Patent
Miller (10) Patent No.: US 7,215,808 B2
(45) Date of Patent: May 8, 2007

(54) HIGH THROUGHOUT IMAGE FOR PROCESSING INSPECTION IMAGES

(75) Inventor: Lawrence R. Miller, Los Altos, CA (US)

(73) Assignee: KLA-Tencor Technologies Corporation, Milpitas, CA (US)

( * ) Notice: Subject to any disclaimer, the term of this patent is extended or adjusted under 35 U.S.C. 154(b) by 217 days.

(21) Appl. No.: 10/860,617

(22) Filed: Jun. 2, 2004

(65) Prior Publication Data

US 2005/0249395 A1 Nov. 10, 2005

Related U.S. Application Data

(60) Provisional application No. 60/568,335, filed on May 4, 2004.

(51) Int. Cl.
G06K 9/00 (2006.01)

(52) U.S. Cl. .................. 382/145; 382/144; 382/152

(58) Field of Classification Search ........ 382/141–152; 712/20; 714/776
See application file for complete search history.

(56) References Cited

U.S. PATENT DOCUMENTS

| | | | |
|---|---|---|---|
| 3,887,762 A | 6/1975 | Uno et al. ............... 178/6 |
| 4,174,514 A | 11/1979 | Sternberg ............ 340/146.3 |
| 4,181,936 A | 1/1980 | Kober ................ 364/200 |
| 4,253,112 A | 2/1981 | Doemens .............. 358/101 |
| 4,445,137 A | 4/1984 | Panofsky ............. 358/101 |
| 4,484,081 A | 11/1984 | Cornyn et al. ........... 250/563 |
| 4,484,349 A | 11/1984 | McCubbrey ............ 382/49 |
| 4,589,140 A | 5/1986 | Bishop et al. ............ 382/8 |
| 4,850,027 A | 7/1989 | Kimmel ............... 382/49 |
| 4,953,224 A | 8/1990 | Ichinose et al. .......... 382/8 |
| 4,979,223 A | 12/1990 | Manns et al. ............ 382/8 |
| 4,984,282 A | 1/1991 | Manns et al. ............ 382/8 |
| 4,985,927 A | 1/1991 | Norwood et al. ........... 382/8 |
| 4,999,785 A | 3/1991 | Schmuter ............. 364/507 |
| 5,001,764 A | 3/1991 | Wood et al. ............ 382/8 |

(Continued)

FOREIGN PATENT DOCUMENTS

WO WO 98/01827 1/1998

(Continued)

OTHER PUBLICATIONS

Goldberg, et al., "Method and Apparatus for Inspecting Reticles Implementing Parallel Processing," U.S. Appl. No. 09/449,022, filed Nov. 24, 1999. 46 pages.

Office Action, dated Oct. 30, 2002, for Goldberg, et al, "Method and Apparatus for Inspecting Reticles Implementing Parallel Processing", U.S. Appl. No. 09/449,022.

Office Action, dated May 8, 2005, for Goldberg, et al, "Method and Apparatus for Inspecting Reticles Implementing Parallel Processing", U.S. Appl. No. 09/449,022.

(Continued)

Primary Examiner—Vikkram Bali
(74) Attorney, Agent, or Firm—Beyer Weaver LLP (57) ABSTRACT

Disclosed is an image processing system for analyzing images of a specimen to determine whether the specimen contains defects. The system includes a plurality of processors for receiving image data from a specimen and for analyzing one or more selected patch(es) of such image data to determine whether the specimen has a defect. The system also includes a plurality of buses for coupling the processors together, wherein the bus has the following specifications: a data rate of about 50 gigabits per second or more and an error rate less than about $10^{-16}$. In one implementation, the buses are low voltage differential signal type buses, and in another implementation, the buses are hyper transport type buses.

20 Claims, 6 Drawing Sheets

U.S. PATENT DOCUMENTS

| | | | |
|---|---|---|---|
| 5,018,212 A | 5/1991 | Manns et al. | 382/8 |
| 5,046,110 A | 9/1991 | Carucci et al. | 382/8 |
| 5,095,447 A | 3/1992 | Manns et al. | 395/161 |
| 5,119,434 A | 6/1992 | Bishop et al. | 382/8 |
| 5,315,700 A | 5/1994 | Johnston et al. | 395/163 |
| 5,355,508 A * | 10/1994 | Kan | 712/20 |
| 5,357,632 A | 10/1994 | Pian et al. | 395/650 |
| 5,434,629 A | 7/1995 | Pearson et al. | 348/721 |
| 5,495,337 A | 2/1996 | Goshorn et al. | 356/376 |
| 5,517,234 A | 5/1996 | Gerber et al. | 348/126 |
| 5,537,669 A | 7/1996 | Evans et al. | 382/141 |
| 5,581,777 A | 12/1996 | Kim et al. | 395/800 |
| 5,608,453 A | 3/1997 | Gerber et al. | 348/87 |
| 5,621,811 A | 4/1997 | Roder et al. | 382/147 |
| 5,659,630 A * | 8/1997 | Forslund | 382/149 |
| 6,081,659 A | 6/2000 | Garza et al. | 395/500.22 |
| 6,130,967 A | 10/2000 | Lee et al. | 382/302 |
| 6,366,687 B1 | 4/2002 | Aloni et al. | 382/144 |
| 6,578,961 B2 | 6/2003 | Vaez-Iravani | 350/237 |
| 6,738,506 B2 * | 5/2004 | Miller et al. | 382/151 |
| 2002/0051565 A1 | 5/2002 | Hiroi et al. | 382/149 |
| 2002/0114506 A1 | 8/2002 | Hiroi et al. | 382/149 |
| 2003/0192006 A1* | 10/2003 | Coakeley et al. | 714/776 |

FOREIGN PATENT DOCUMENTS

WO      WO 00/68884 A1 * 11/2000

OTHER PUBLICATIONS

Office Action, dated Jul. 29, 2003, for Goldberg, et al, "Method and Apparatus for Inspecting Reticles Implementing Parallel Processing", U.S. Appl. No. 09/449,022.

Office Action, dated Jan. 23, 2004, for Goldberg, et al, "Method and Apparatus for Inspecting Reticles Implementing Parallel Processing", U.S. Appl. No. 09/449,022.

Office Action, dated Jul. 1, 2004, for Goldberg, et al, "Method and Apparatus for Inspecting Reticles Implementing Parallel Processing", U.S. Appl. No. 09/449,022.

Office Action, dated Apr. 29, 2005, for Goldberg, et al, "Method and Apparatus for Inspecting Reticles Implementing Parallel Processing", U.S. Appl. No. 09/449,022.

* cited by examiner

HIGH THROUGHOUT IMAGE FOR PROCESSING INSPECTION IMAGES

CROSS REFERENCE TO RELATED PATENT APPLICATION

This application claims priority of U.S. Provisional Patent Application No. 60/568,335, entitled HIGH THROUGHPUT IMAGE FOR PROCESSING INSPECTION IMAGES filed 4 May 2004 by Lawrence R. Miller, MD, PhD, which application is incorporated herein by reference in its entirety for all purposes.

BACKGROUND OF THE INVENTION

The present invention relates generally to the field of semiconductor inspection. More specifically, it relates to techniques for processing inspection images and the like.

Generally, the industry of semiconductor manufacturing involves highly complex techniques for fabricating integrating circuits using semiconductor materials which are layered and patterned onto a substrate, such as silicon. Due to the large scale of circuit integration and the decreasing size of semiconductor devices, the device must be defect free prior to shipment of the device to the end users or customers. Thus, the resulting device or wafer needs to be inspected for defects. Additionally, the reticles which are used to fabricate the wafers are also inspected for defects.

A reticle or photomask is an optical element containing transparent and opaque, semi-transparent, and phase shifting regions which together define the pattern of coplanar features in an electronic device such as an integrated circuit. Reticles are used during photolithography to define specified regions of a semiconductor wafer for etching, ion implantation, or other fabrication process. For many modern integrated circuit designs, an optical reticle's features are between about 1 and about 5 times larger than the corresponding features on the wafer. For other exposure systems (e.g., x-ray, e-beam, and extreme ultraviolet) a similar range of reduction ratios also apply.

Optical reticles are typically made from a transparent medium such as a borosilicate glass or quartz plate on which is deposited on an opaque and/or semi-opaque layer of chromium or other suitable material. However, other mask technologies are employed for direct e-beam exposure (e.g., stencil masks), x-ray exposure (e.g., absorber masks), etc. The reticle pattern may be created by a laser or an e-beam direct write technique, for example, both of which are widely used in the art.

After fabrication of each reticle or group of reticles, each reticle is typically inspected by illuminating it with light emanating from a controlled illuminator. Optical images of one or more portions of the reticle are constructed based on the fraction of the light reflected, transmitted, or otherwise directed to a light sensor. Such inspection techniques and apparatus are well known in the art and are embodied in various commercial products such as many of those available from KLA-Tencor Corporation of San Jose, Calif.

During a conventional inspection process, the optical image of the reticle portion being inspected is typically compared to a corresponding reference image. Conventionally, the reference image is either generated from a circuit pattern data that was used to fabricate the reticle or from an optical image of a nearby area of the reticle itself. Either way, the optical image features are analyzed and compared with corresponding features of the reference image. Each feature difference is then typically compared against a threshold value. If the optical image feature varies from the test feature by more than the predetermined threshold, a defect is defined. A similar inspection process may also be used to inspect a semiconductor wafer which is fabricating using a plurality of reticles.

Mechanisms for a typical inspection process may include a number of serially coupled processors. The image data is fed into and processed by a first processor. After the first processor performs one step of the analysis, the resultant data is then fed into a second processor for the next step in the analysis. The image data may be fed serially into any number of processors. Typically, the different processors will each perform some small portion of the total analysis algorithm(s). The algorithms are usually hard-coded into the individual processors.

Although serially processing portions of the image data is adequate for some applications, it is too slow and/or inflexible under certain conditions. For example, as circuit patterns and corresponding reticle patterns grow more complex, the image data of such reticles grows to contain a relatively large amount of data that must be accurately analyzed. A typical reticle may be converted into 1 million by 1 million pixels of image data. Thus, it may become quite burdensome to process such large amounts of image data.

Additionally, conventional image processing is often dependent on the proper functioning of all of the processors. That is, if a single processor fails within the serial chain of processors, the image data may not be properly analyzed. The inability to properly analyze is especially likely if there are no other processors within the serial chain of processors that perform the failed processor's functions.

Finally, inspection systems that include processors with fixed or hard-coded algorithms often cannot handle the full range of possible algorithms that may be useful for image processing, and they are not easily upgraded or changed if a new set of algorithms is desired. For example, if new algorithms are desired, the processors may have to be replaced with new processors that have a new set of hard-coded algorithms. This procedure may be relatively time-consuming and/or costly.

Thus, improved inspection apparatus and techniques are needed. More specifically, mechanisms for more efficiently and accurately processing image data are desired.

SUMMARY OF THE INVENTION

In one embodiment, an image processing system for analyzing images of a specimen to determine whether the specimen contains defects is disclosed. The system includes a plurality of processors for receiving image data from a specimen and for at least a subset of the processors each analyzing one or more selected patch(es) of such image data to determine whether the specimen has a defect. The system also includes a plurality of buses for coupling the processors together, wherein the bus has the following specifications: a data rate of about 50 gigabits per second or more and an error rate less than about $10^{-16}$. In one implementation, the buses are low voltage differential signal type buses, and in another implementation, the buses are hyper transport type buses.

In a specific embodiment, the processors coupled together with the buses into a serial chain so that the processors sequentially receive the image data and analyze selected one or more patch(es) of such image data. The processors are further operable to output one or more result signal(s) indicating whether the specimen has defects after analyzing their selected patch(es), and the result signal(s) of each processor are output with the image data. In a further aspect, at least one of the buses passes between two boards that each contain one or more processors.

In another embodiment, the processors are arranged in a two level hierarchical arrangement so that one or more processors each referred to as a distributor are associated with a set of processors referred to as analyzing processors. Each distributor is operable to distribute a selected one or more patch(es) to each analyzing processor in its associated set for analysis of such distributed patch(es). In a further aspect, at least one of the buses passes between two boards that each contain one or more processors. In yet a further aspect, the processors include a single distributor for distributing one or more image patch(es) to each of a plurality of four associated analyzing processors, and each of the four analyzing processors receives a quarter of the image data from the specimen.

In a specific implementation, the processors include a first distributor for distributing one or more image patch(es) to each of a plurality of four associated analyzing processors for analysis of such distributed patch(es) and a second distributor for distributing one or more image patch(es) to each of a plurality of four associated analyzing processors for analysis of such distributed patch(es). Each of the eight analyzing processors receives an eighth of the image data from the specimen.

In a further embodiment, the system further includes a host for analyzing and/or displaying defect data, wherein each analyzing processor is also operable to output one or more results signal(s) to the host, the result signal(s) indicating whether the specimen has a defect. In another aspect, the system includes a clock module for generating a master clock for use by the processors and a pixel clock for defining pixels within the image data with respect to an angle clock of the inspection tool used for collecting the image data from the specimen. In a specific implementation, the image data is collected from a rotating specimen and the pixel clock and synchronization signals are generated so that pixel resolution is altered according to a radial position of the specimen so as to obtain a substantially constant pixel resolution along the radius. The synchronization signals indicate a relative position of the pixel clock with respect to the master clock.

In one embodiment, the image data corresponds to a plurality of semiconductor dies and at least one or more of the processors are operable to generate a reference die based on an average of a portion of the dies of the image data and wherein one or more same or other processors are operable to compare the reference die to other dies in its image patch(es) to determine whether the specimen has a defect.

In an alternative embodiment, the invention also pertains to an image processing system for analyzing images of a specimen to determine whether the specimen contains defects. This system includes a plurality of inspection signal processors for receiving different sets of optical signals obtained from an inspection tool while inspecting a specimen. Each inspection signal processor is operable to convert its received set of optical signals into digital image data and output such image data at a particular time slot of a master clock sent to a next inspection signal processors if present. The system further includes a distributor processor for receiving the image data from the plurality of inspection signal processors and for dividing the image data into a plurality of image patches and a plurality of analyzing processors associated with the distributor. The distributor is further operable distribute selected image patches to selected analyzing processors for parallel processing to determine whether the specimen has a defect.

In a further aspect of this alternative embodiment, the distributor receives the image data from a last one of the inspection signal processors after all of the inspection signal processors have contributed to the image data. In a specific implementation, there are 12 inspection signal processors and eight analyzing processors. In a further aspect, there are two inspection signal processors per board, the distributor and associated analyzing processors are one a single board, and the inspection signal processors and the distributor are serially coupled together by a high speed bus having the following specifications: a data rate of about 50 gigabits per second or more and an error rate less than about $10^{-16}$. In one embodiment, the high speed bus is a low voltage differential signal type bus.

In one aspect, the analyzing processors are each further operable to send a signal to the inspection tool indicating that the inspection tool needs to decrease its image data output speed when the speed is greater than the each analyzing processor can process its image patch(es). In another aspect, the optical signals are received in the form of annular swaths of the specimen. Alternatively, the optical signals are received in the form of rectangular swaths of the specimen.

These and other features and advantages of the present invention will be presented in more detail in the following specification of the invention and the accompanying figures which illustrate by way of example the principles of the invention.

DETAILED DESCRIPTION OF SPECIFIC EMBODIMENTS

Reference will now be made in detail to a specific embodiment of the invention. An example of this embodiment is illustrated in the accompanying drawings. While the invention will be described in conjunction with this specific embodiment, it will be understood that it is not intended to limit the invention to one embodiment. On the contrary, it is intended to cover alternatives, modifications, and equivalents as may be included within the spirit and scope of the invention as defined by the appended claims. In the following description, numerous specific details are set forth in order to provide a thorough understanding of the present invention. The present invention may be practiced without some or all of these specific details. In other instances, well known process operations have not been described in detail in order not to unnecessarily obscure the present invention.

Figure 1:
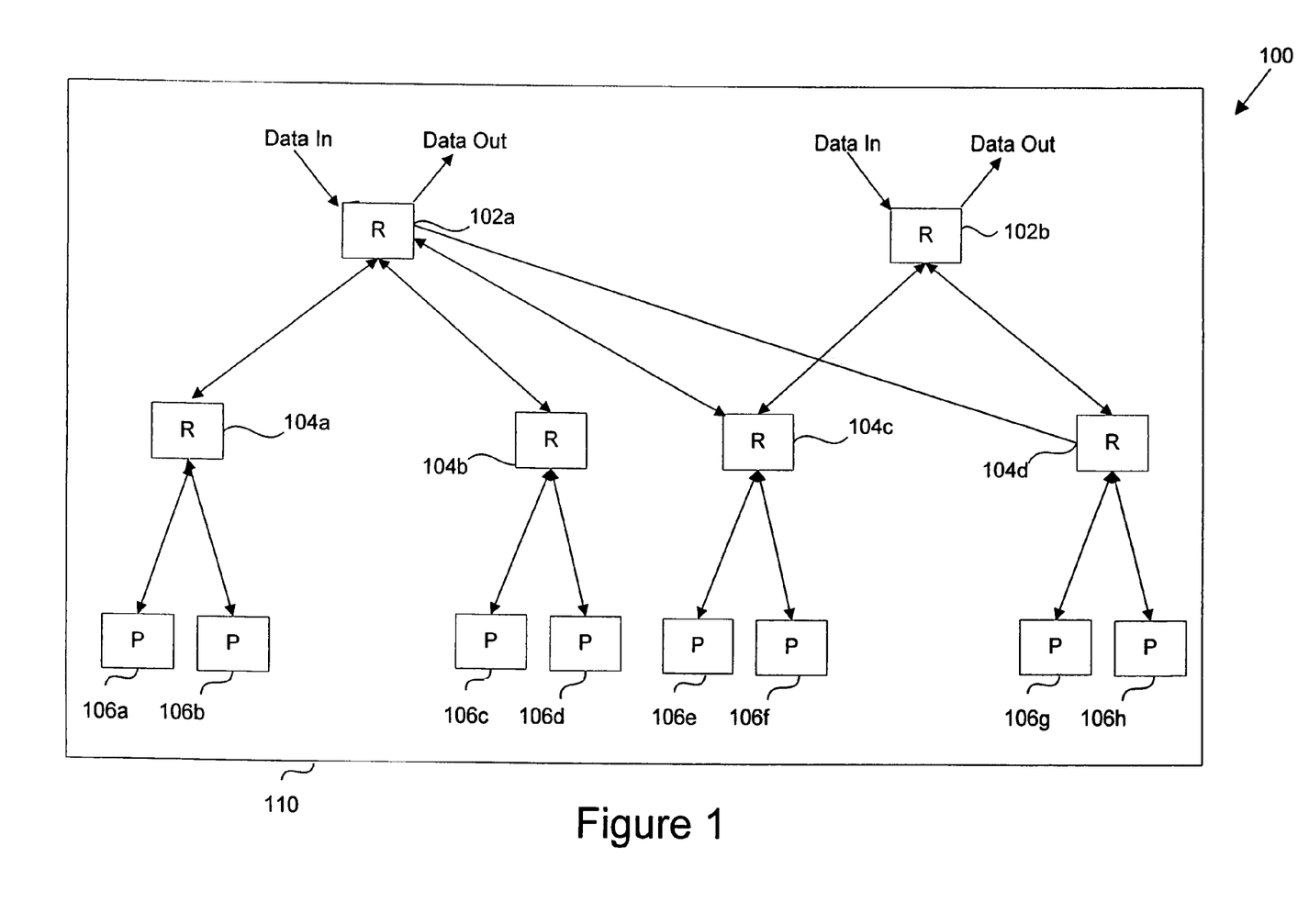
FIG. 1 is a diagrammatic representation of one system approach for processing image patches in a plurality of parallel processors.

FIG. 1 is a diagrammatic representation of one system approach for processing image patches in a plurality of parallel processors. In this approach, a plurality of data routers 102 and 104 are arranged hierarchically with a plurality or processors 106. Several embodiments of such a hierarchical system are further described in U.S. application Ser. No. 09/449,022, entitled METHOD AND APPARATUS FOR INSPECTING RETICLES IMPLEMENTING PARALLEL PROCESSING, filed 24 Nov. 1999 by Goldberg et al., which application is incorporated herein by reference in its entirety for all purposes.

In this implementation, a top router is configured to pass only a portion of the image data stream to its lower routers, and these lower routers are then configured to pass individual image patches to a individual processors. Each processor is then operable to perform inspection analysis on its own received patches, e.g., by performing a die to die comparison on dies positioned in one or more patches. For instance, router 102a receives a first set of patches, and router 102b receives a second set of patches. Router 102a then divides its set of patches into two set of patches which are each passed to its lower routers 104a and 104b. Likewise, router 102b divides its own set of patches into a first and second set of patches which are routed to its underlying routers 104c and 104d, respectively. Finally, lower router 104a then sends selected patches to either processor 106a or 106b. Lower routers 104b, 104c, and 104d also send selected patches to their underlying processors.

This arrangement may be a mesh type scheme, where the routers are coupled together in a more complex manner. For example, upper router 102a may also be configured to route image patch sets to underlying router 104c. Other connections between upper and lower routers, as well as between lower routers and processors may also be present, besides those connections illustrated in FIG. 1.

When the routers and processors are general purpose programmable routers and processors, the data steam rate becomes an issue. Currently available general purpose routers and processors are not able to route or process data at a fast enough rate to keep up with inspection data output rates from the scanner or inspection tool.

Since the entire image data stream is passed between the top routers, the bus rate between the top routers generally has to be high. The bandwidth rate between the top and lower routers and between the lower routers and the processors can remain low since only a portion of the data stream is handled. Although fast buses have been used on a single board (e.g., 110 of FIG. 1), there currently exists no solution for delivering high rate data between boards. As a result of this limitation of high speed buses to single board processors, this type of hierarchical, mesh image processing system is typically fixed as to the number of processors on a single board and not easily scalable. That is, the processing board would have to be completely redesigned to add processing power to the system.

In general terms, the present invention provides an expandable, high speed image processing system, where image data is efficiently passed between sets of processors whose numbers are expandable at a rate that is at least as high as the inspection tool output data rate. Although the systems of the present invention are described herein in relation to inspection image processing, the inventive systems of the present invention are also applicable to processing other types of image data, such as data from a metrology tool, etc.

In one implementation of an imaging processing system, image data is passed between processors or routers on multiple boards using a bus that can transmit at a data rate that is at least as fast as the rate of the image data as collected and output by the inspection tool. Preferably, the bus allows the image data to be transmitted on high density signal lines having minimum interference properties and low cost. Preferably, the bus has the following specifications: a data rate of about 50 gigabits per second or more and an error rate less than about $10^{-16}$. One such bus is a Low Voltage Differential Signal (LVDS) bus. Alternatively, a hyper transport bus may be utilized or any suitable low interference, high speed bus type. An LVDS bus typically utilizes two lines for each signal (e.g., image pixel), and each signal is represented by a low voltage potential, such as 0.4 V, between each line pair for a "1" binary value and 0.0 V for a "0" binary value. The system embodiments of the present invention include other novel features described further below, which can be used alone or in conjunction with this high speed bus feature.

Figure 2:
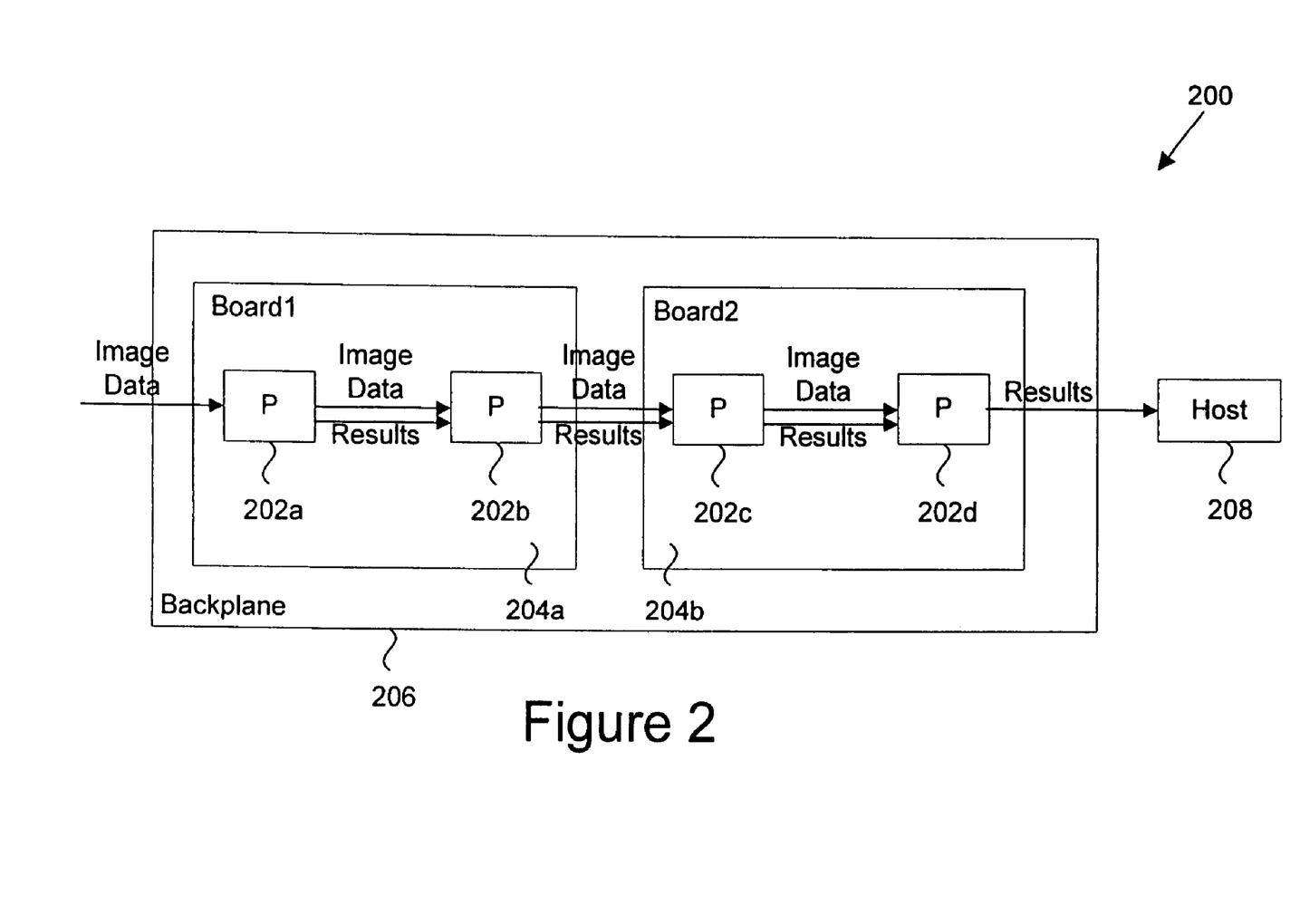
FIG. 2 is a diagrammatic representation of an imaging system in accordance with a first embodiment of the present invention.

FIG. 2 is a diagrammatic representation of an imaging system 200 in accordance with a first embodiment of the present invention. As shown, image data is received by a first processor 202a of a first board 204a. This first processor analyzing a first portion of this image data, while passing the entire image data and processing results from the first image portion to a second processor 202b on the same first board 204a. Of course, each board may include any number of processors. The second processor 202b of the first board 204a then processes a second portion of the image data and transmits the results of such processing and the entire image data to a first processor 202c of a second board 204b. The first processor 202c of the second board then processes a third image portion and sends the processing results and entire image data to the second processor 202d of a second board 204b.

Signals are passed between the processors and processor boards using a high speed bus on backplane 206, such as the LVDS, that has at least a same data rate as the image data output from the inspection tool. The last processor 202d of the last board 202b then sends the results to a host 208 that is configured to store the results data to one or more databases or persistent memory devices and/or display the results data to a user. The host 208 may also be configured to perform further analysis on the results data, e.g., classify a defect, determine root cause of a defect, etc. Any number of processing boards may be appended or coupled to the existing series of processing boards to expand the processing power of the system 200.

The processors of the arrangement of FIG. 2 can be any suitable combination of hardware and/or software for processing patches of the imaging data and sending the imaging data and results data to a next processor. In one low cost implementation, the processors are general purpose processors, such as the 6414 processors available from Texas Instruments of Dallas, Tex. In sum, this processing and bus arrangement 200 provides a high speed parallel image processing system that is readily scalable due to the use of multiple processing boards and high speed buses there between.

Figure 3:
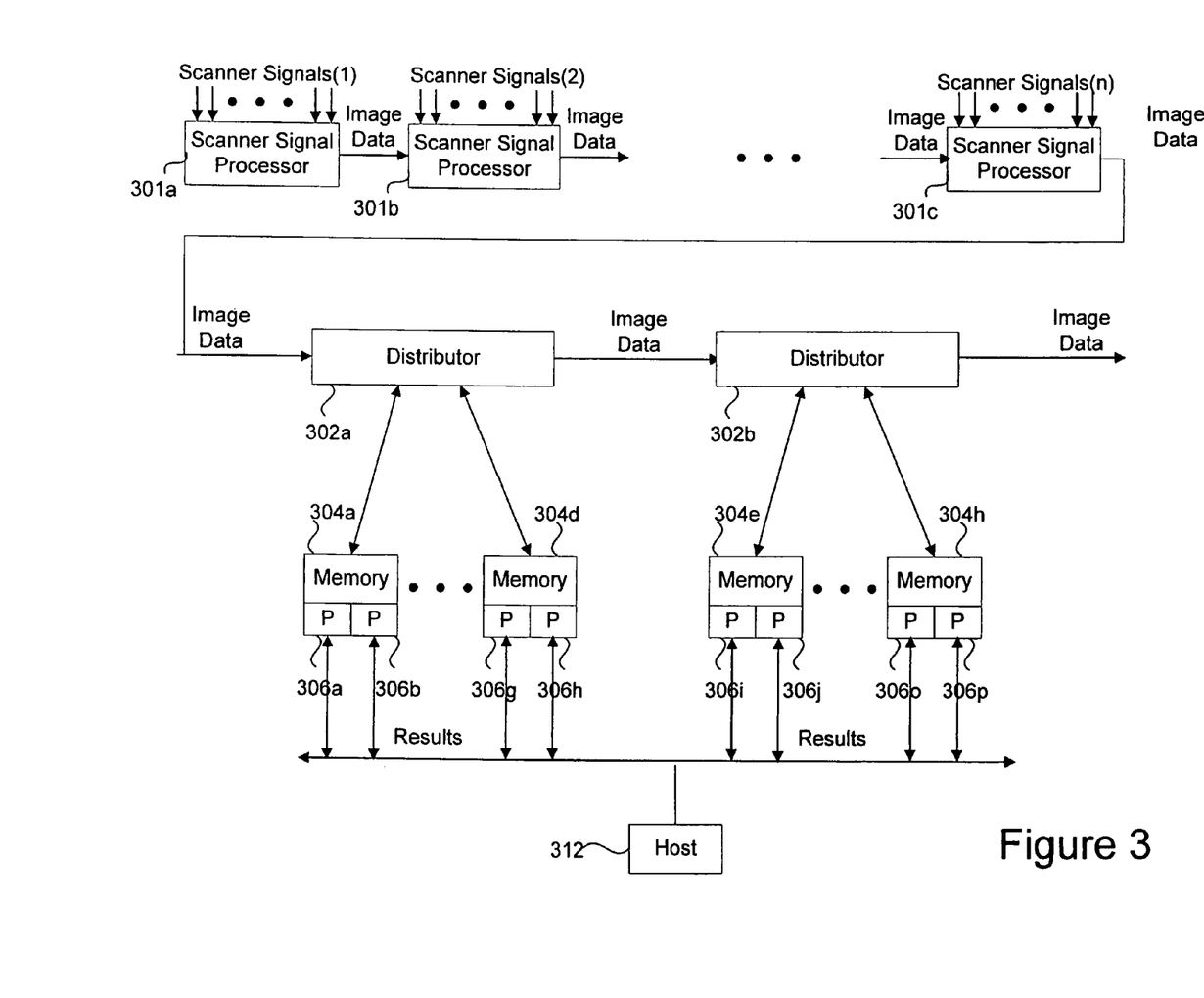
FIG. 3 is a diagrammatic representation of an imaging system in accordance with a second embodiment of the present invention

FIG. 3 is a diagrammatic representation of an imaging system 300 in accordance with a second embodiment of the present invention. In general, the system 300 is a two level daisy chain type system which also utilizes multiple processing boards with high speed buses between the processors and boards. As shown, the system 300 may include a plurality of scanner signal processors 301 for receiving scanner signals output by a scanner or inspection tool. Each scanner signal processor 301 receives a particular number of scanner signals and outputs its received scanner signals in a digital format in a particular time slot of an image data bus or "daisy chain" bus, which is passed to a next scanner signal processor that is operable to do the same with its own scanner signals, etc., as further described below.

The system 300 further includes one or more distributors 302 through which the image data is passed. Each distributor is configured to acquire a different set of image patches from the image data for processing by a selected set of underlying servers. In other words, each distributor operates to buffer and distribute a portion of the image data. For instance, distributor 302a acquires images from a first half of a semiconductor wafer for processing by a first set of servers, while distributor 302b acquires image patches from a second half of the wafer for processing by a second set of servers.

In the illustrated implementation, the servers associated with each distributor each include memory 304 and two processors 306. Of course, each server may include any number of memory devices and/or processors, and the illustrated example is not meant to limit the scope of the invention. Additionally, any number of processors may share one or more memory devices. In one embodiment, each server processes a portion of its distributor's acquired image data portion and sends results to host 312, which is similar in function to the host 308 of FIG. 2, through any suitable interface bus such as Ethernet. For example, each processor 306a through 306d processes a quarter of the image portion acquired by distributor 302a, while each processor 306e through 306h process a quarter of the image portion acquired by distributor 302b.

To facilitate expansion, the distributors are preferably each arranged on a board, and the boards are coupled together on a backplane as further described below. The high speed image data is passed between each distributor board using a high speed bus, such as a LVDS bus. Likewise, any number and type of servers may be arranged on any number of boards. The results bus does not have to be high speed since it is merely passing results data, which typically has a low band width.

Figure 4:
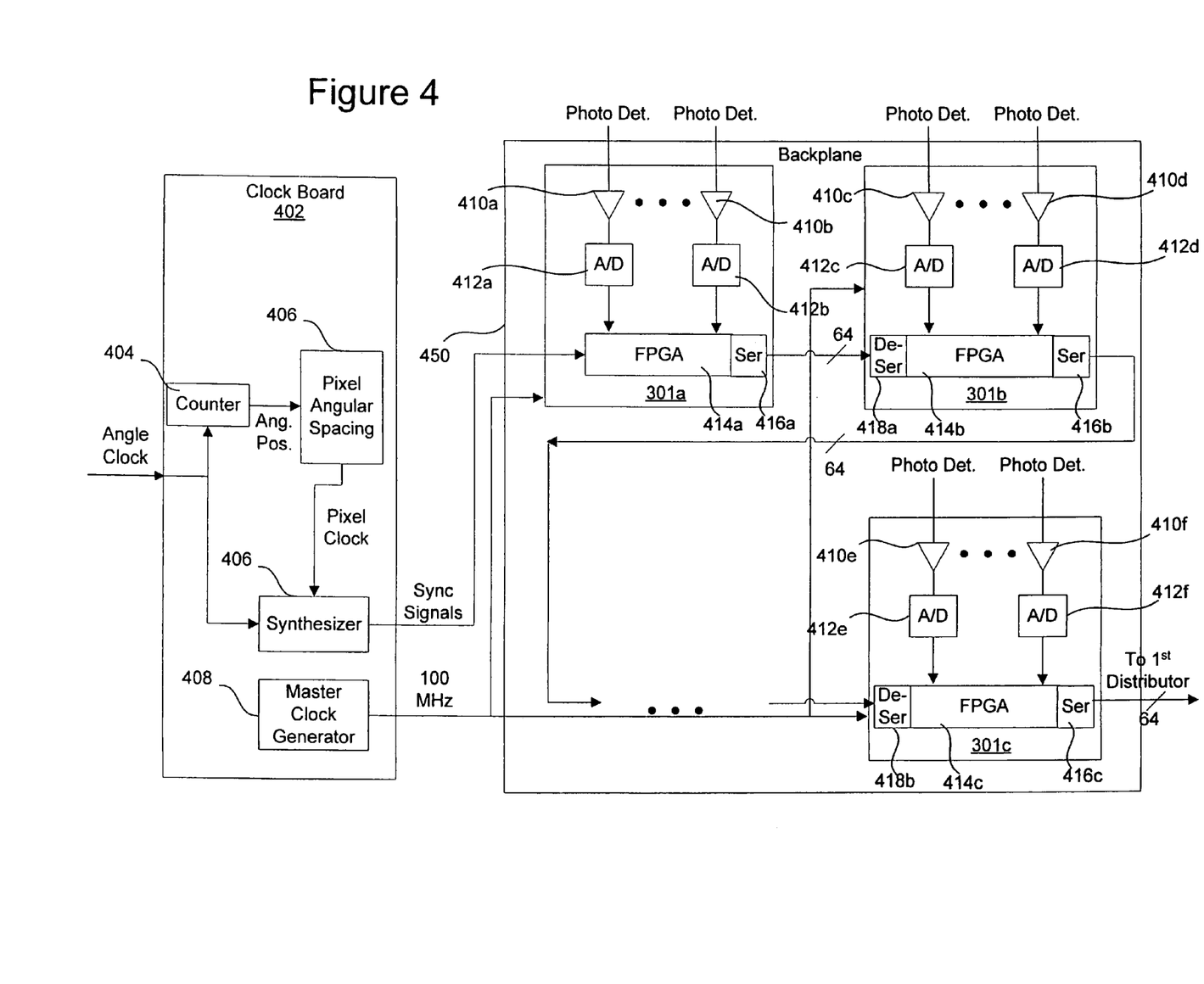
FIG. 4 is a diagrammatic representation of the scanner signal processors of FIG. 3 and a clock board for feeding timing signals to such processors in accordance with a specific implementation of the present invention.

FIG. 4 is a diagrammatic representation of the scanner signal processors 301 of FIG. 3 and a clock board 402 for feeding timing signals to such processors 301 in accordance with a specific implementation of the present invention. In one implementation of a scanner or inspection tool, a rotating scanner collects image data from a wafer in a spiral pattern. That is, the wafer is rotated relative to the optical signal which is directed towards the wafer to thereby collect detected optical signals from the wafer. This rotating scanner can include an optical encoder and PLL electronics for generating a high frequency signal or "Angle Clock". The angle clock generally provides a mechanism for determining the current position of the wafer, e.g., the angle clock gives a fixed number of pulses per a specific angle of rotation of the wafer. The number of angle clock pulses may be counted from the initiation of the scan to obtain the current angular position of the specimen or wafer. Thus, the clock board 402 may include a counter 404 for counting the angle clock pulses and outputting an angular position or count which correspond to an angular position of the specimen.

It also may be desirable to define a pixel within the collected image data at known angular positions of wafer, but not necessarily at positions of the optical encoder. In one embodiment, a synthesizer is used to simulate a pixel clock for defining pixels in the image data stream and the pixel clock pulses correspond to particular angular wafer positions. A pixel clock cycle is output so as to correspond to a known number of whole or fractional angle clock counts. Preferably, the differential in angular speed of different radial positons of the wafer is taken into account to generate the pixel clock. For instance, as the scanner moves from the outer to the inner part of wafer, an angular spacing block 406 operates to generate fewer pixel pulses per the specific angle. In other words, the pixel resolution is altered according to radial position so as to obtain a substantially constant pixel resolution with respect to the radius.

Figure 6:
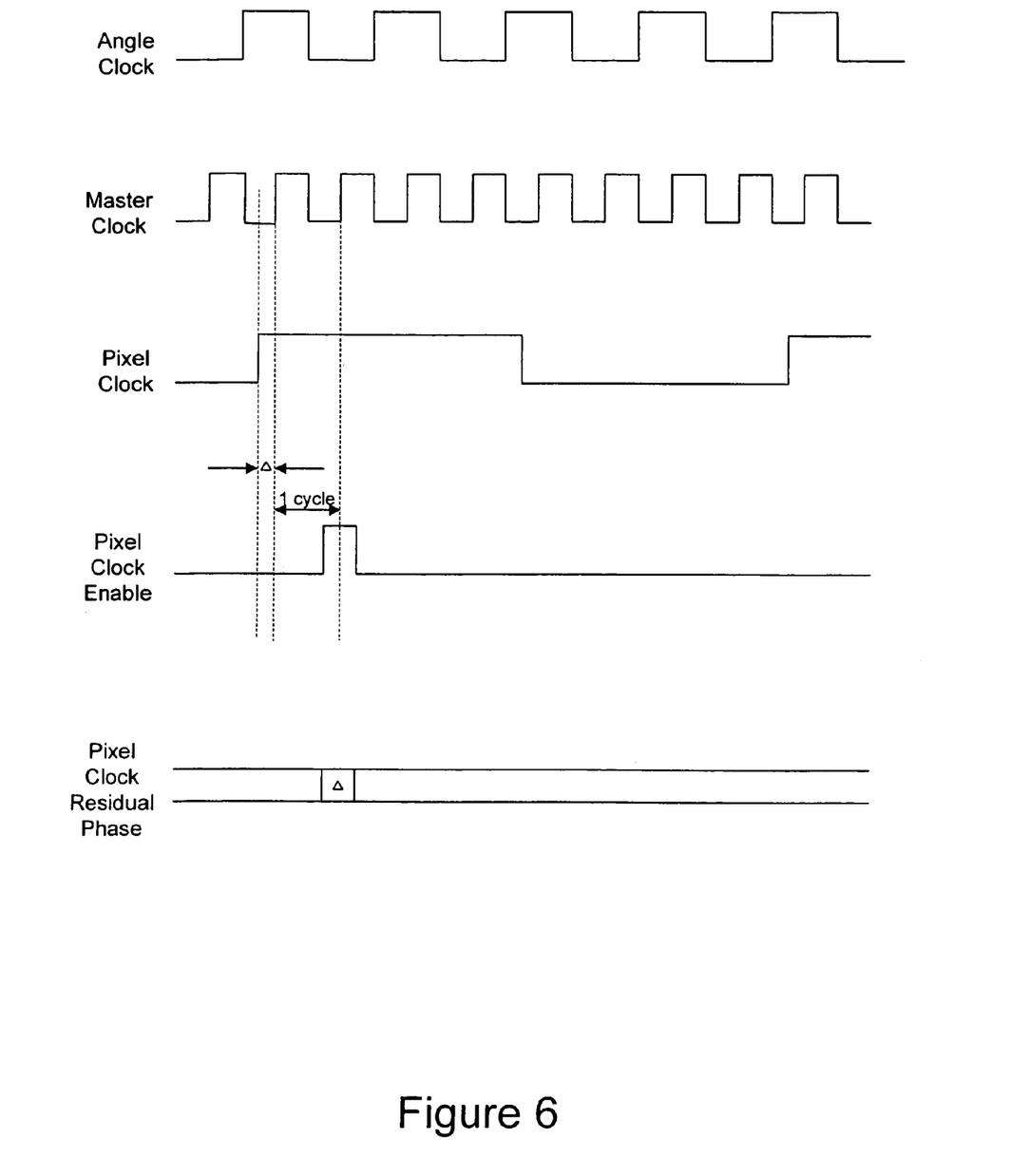
FIG. 6 illustrates graphical representation of example timing signals used and/or generated in embodiments present invention.

In one embodiment, the pixel clock is not at a known phase with respect to the master clock used by the imaging system. Thus, in this example, the pixel clock is converted to an enable signal sampled at the master clock rate (e.g., 100 MHz). It should be noted that the pixel clock may not be phase-tied to either the angle clock or the master clock. FIG. 6 illustrates an example Angle Clock, Master Clock, and Pixel Clock. Accordingly, a the clock board 402 may also be configured to generate synchronization signals for indicating a relationship between the pixel clock and the master clock. As shown, the clock board 402 includes Synthesizer 406 for generating a pixel clock enable and a pixel clock residual phase signal (see Pixel Clock Enable and Pixel Clock Residual Phase signals of FIG. 6) for indicating a relative position of the pixel clock with respect to the master clock. The pixel clock enable signal samples the pixel clock when it is high. However, the pixel clock enable signal is preferably delayed from a rising edge of the pixel clock by at least a full master clock cycle. The clock residual phase signal or "delta" represents the distance to the next rising edge of the master clock from a rising edge of the pixel clock, and this delta can vary. In this embodiment, the pixel clock enable signal is centered around the next rising edge of the master clock which occurs after delta plus a full master clock cycle.

To explain further, the processors which analyze the pixels need to know the position of their master clock with respect to the pixel clock, which was generated from the angle clock of the inspection tool (unless, of course, the angle clock is used as the master clock or to generate a master clock). Thus, the pixel clock enable and clock residual phase signal are input to the image processing components of the illustrated system.

The analog to digital (ADC) converters which process the image stream may be run to sample the image stream when the pixel clock pulses occurs. However, it is difficult to synchronize a high number of ADC's as used in embodiments of the present invention. To get around this problem, the ADC's which process the image stream are run to sample the image stream at any suitable frequency, such as a 100 MHz master clock rate. An interpolation is then done (e.g., by a field programmable gate array or FPGA) to interpolate the stream of sample pixels to produce a 12 bit digital value that corresponds to what would have been produced if the scanner clock (e.g., angle clock) would have been sampled right at the pixel clock. When a master clock which differs from the scanner clock is used, the interpolator needs to know the nearest master clock rising edge, as well as the residual phase error. In the present embodiment, a four bit bus is used to output the residual phase error or delta to the image processing components as synchronization signals.

In one implementation, the residual phase error and pixel enable signals travel on the daisy chain between each set of processors, along with the image data and results. Since in this example there are slightly less bits needs on the daisy chain for the pixels output from the scanner, the sync signals reside on the unused bits. Thus, each processor knows when the pixel clock rising edge is to come. Of course, there will be a delay between each set of processors or boards, but this delay is fixed and known by each processor. Thus, a sample of the image data may be obtained at the pixel clock even though the ADC's are run at a different rate. In comparison, a jitter of one clock cycle would be produced if the nearest sample was obtained instead of performing an interpolation.

As shown in FIG. 4, each scanner signal processor board 301 receives ten optical channels and contribute ten pixels to the daisy chain bus. Of course, each board 301 may process any number of optical channels and corresponding pixels. As shown, each channel is input into a preamplifier 410 and then through an analog to digital converter (ADC) for generating a digital signal from the input channel signal. The channel signals are then processed any suitable type of hardware and/or software processor, such as FPGA 414, to result in a bit stream of image data output on the daisy chain bus at the master clock rate to the next signal processor board 301. For instance, signal processor board 301a outputs the image data onto a daisy chain bus to signal processor board 301b.

In the present invention, the full daisy chain bus which is present between each board holds 120 pixels. In one implementation, one frame time is reserved for each set of two boards. In the illustrated example, there are 12 boards which utilize a total of six frames. Each master clock cycle may be utilized to hold one frame, and, accordingly, six cycles will hold the entire six frames of image data. Each set of boards is configured to know at which cycle half to output its data onto the daisy chain bus. Otherwise, each set of boards simply copies the image data it receives from a previous set of boards in the daisy chain bus at the cycles at which the image data was received. Said in another way, each set of boards adds its own image data to the appropriate cycle half of the daisy chain bus.

In contrast to the above described synchronous pixel processing embodiments, conventional image processing systems run asynchronously. Each pixel conversion generates an asynchronous packet that is output onto a network. This type of system requires a complex network protocol and is inherently slower then preferred embodiments of the present invention. An asynchronous pixel processing system also requires network transceivers and fiber, resulting in higher associated costs.

Figure 5:
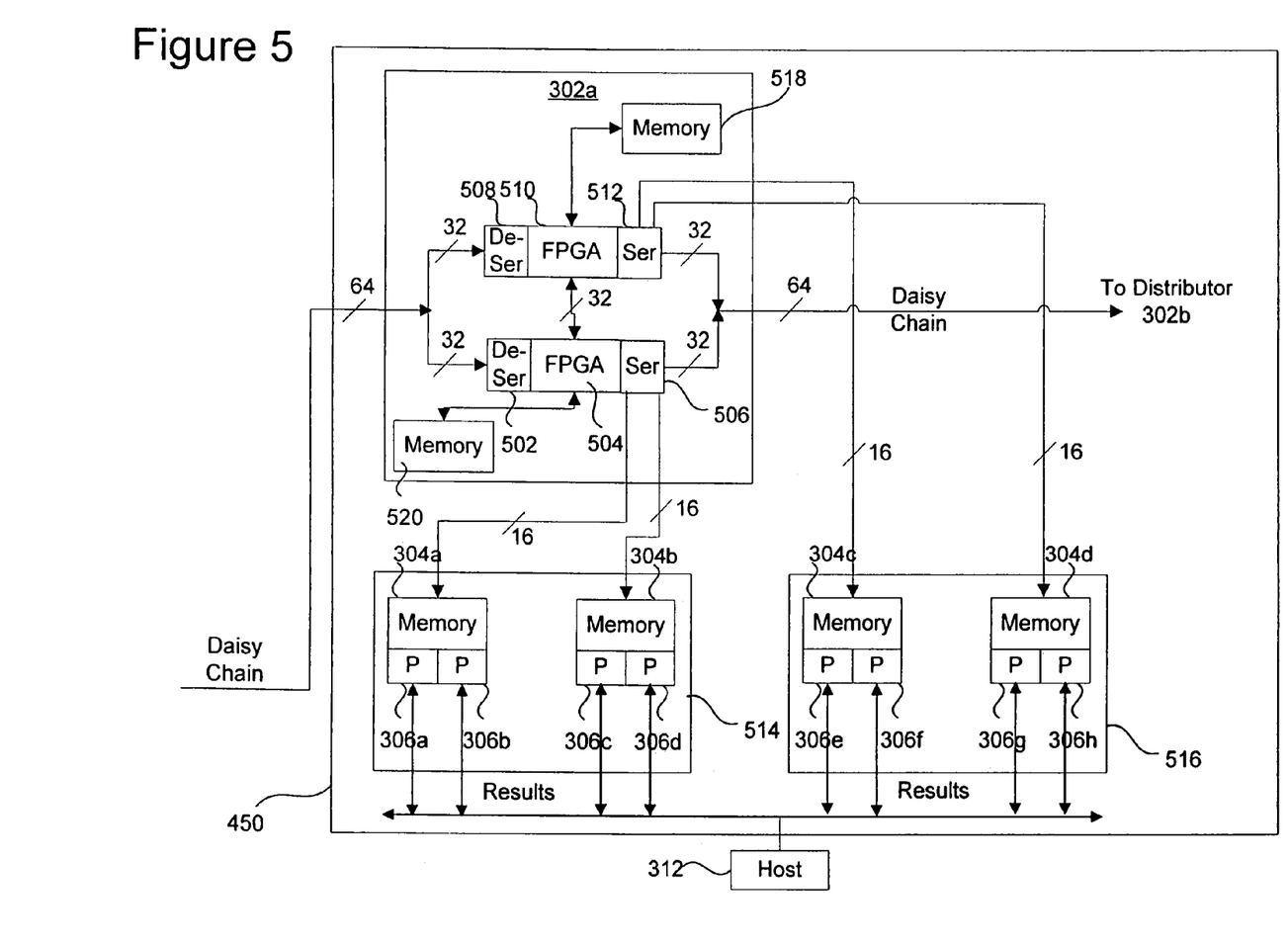
FIG. 5 is a diagrammatic representation of the first distributor and its associated processors in accordance with one embodiment of the present invention.

The daisy chain is output from the last scanner signal processor (e.g., 301c of FIG. 3) into the first distributor 302a. FIG. 5 is a diagrammatic representation of the first distributor and its associated processors in accordance with one embodiment of the present invention. In this implementation, this output signal includes 64 bits at 400 MHz (or four times the master clock rate) which are divided into a first and second set of 32 bit bus. A pair of FPGA's 510 and 502 may then each receive a one of the 32 bit buses. Each FPGA divides the image data into four 16 bit buses and sends each 16 bit bus to a selected on of the servers 304a, b, c, or d. As each FPGA receives the 32 bit image data, the image data is de-serialized for processing and then serialized prior to outputting the data back onto the daisy chain where the two 32 bits are combined into a 64 bit bus. In other words, the FPGA may be configured to process the entire 128 bits of data together, which was received into the FPGA in a format having four successive 64 bit of image data at 400 MHz. That is, the image data was compressed from 256 bits at 100 MHz to four series of 64 bits at 400 MHz. As shown in the illustrated example, FPGA 510 has deserializer 508 and FPGA 504 has deserializer 502. Likewise, FPGA 510 has serializer 512 and FPGA 504 has serializer 506.

Of course, the any suitable mechanism, besides an FPGA, may be used to divide and distribute the data to the individual servers or processors and any suitable division of the image, besides 16 bit, as well as serialization technique may be utilized. In the present implementation, the 64 bit daisy chain bus is divided into two 32 bit buses because each FPGA has only 64 channels (32 for input and 32 for output). Of course, the daisy chain bus may be divided differently if a FPGA or other component with a different number of channels was used. Additionally, a 64 bit daisy chain is used since this number of LVDS lines may be readily grouped together on the boards used by the present invention system. Any suitable daisy chain size may be used.

Each FPGA preferably has associated memory for storing the received image data. As shown, FPGA 510 has associated memory 518, while FPGA has associated memory 520. In one embodiment, one wafer revolution of image data is buffered by the memory 518 and 520. A 1 GByte DDR SDRAM (double data rate synchronous dynamic RAM) works well in current applications although any suitable memory type and size may be utilized, depending on the particular application requirements.

The FPGA's are programmed to divide the image data into patches which are then each sent to a selected server. Each patch may be formed to have any suitable size and shape which can be processed by a server to determine defects. In one example, each patch has an area that is large enough to contain whole dies that can be compared in a die-to-die inspection procedure. In this example, the image data of the entire wafer may be divided into four sectors or quadrants, and each patch corresponds to a single quadrant. Each quadrant or patch of data may then be handled by a single distributor having four servers, which each process a one of the quadrants. The image data may alternatively be divided further into 8 sectors, which are handled by two distributors each having four servers (as in the illustrated embodiment). The image data can be divided into any suitable number of sectors. In an alternative embodiment, the image data is simply divided into rectangular patches.

In the four quadrant example, each FPGA (504 or 510) uses its associated memory (520 or 518) to store 32-bit portions of the image data as it is input into the distributor. In one implementation, one revolution of image data is stored at a time into two memory by the FPGA. Each FPGA may have any suitable number of associated memory. Each FPGA (504 or 510) of each distributor 301 may be generally operable to then output one or more particular patch(es) (e.g., a half portion or two quadrants of the wafer image data) to the appropriate server. Thus, the FPGA of the distributors may need to communicate with each other (e.g., via a 32 bit bus) to access the image data stored in each other's memory for sending to its associated servers. In the illustrated embodiment, each distributor FPGA sequences the image data for distribution to each server. For example, a sequencing table is hard coded in each distributor FPGA (e.g., by host 312).

If there are multiple distributors, the distributor boards 302 may be coupled via the daisy chain bus on a backplane 450. Each distributor may also be coupled to a plurality of servers 304 via a plurality of multiple bit buses on backplane 450. Examples of a high speed bus which work well are a LVDS and a hyper transport bus.

Each server may include one or more memory and one or more processors. In the illustrated example of FIG. 5, each server includes a common memory and two processors. Additionally, each distributor may be associated with any number of servers. In the illustrated embodiment, each distributor is associated with four servers. As shown in FIG. 5, distributor 302a is coupled with servers 304a through 304d. Server 302a includes memory 304a and processors 306a and 306b; server 302b includes memory 304b and processors 306c and 306d; server 302c includes memory 304c and processors 306e and 306f; and server 302d includes memory 304d and processors 306g and 306h.

A pointer to the end of the image data is also given to each processor (e.g., by the distributor FPGA's) as the server memory is filled. Since in the illustrated embodiment the image data also includes the pixel clock and coordinate data, which indicate an angular and radial position of each pixel, and each frame size is known, each processor can determine where each set of image data for a particular wafer position is located in the server memory and analyze portions of its own image patch (when there is enough image data to analyze).

Each processor 306 generally operates to process its own image patch (e.g., quadrant) to determine whether defects are present in such patch. The results may then be output to host 312 which can operate to display the results, e.g., graphically, in a table or visually. The results may take any suitable form for indicating that a particular patch has a defect. For example, the results may include an image of the defect and its coordinates. The host 312 (or alternatively each processor) may also be configured to further analyze the defect, such as classify the defect, determine lot deposition, determine whether there is a process excursion, determine the root cause of a defect, etc.

Each processor may also be programmed to send a signal back to the scanner to indicate whether image data is being received to quickly for the processor to analyze it before its server memory is overwritten. Ideally, another distributor and more processors would be utilized to speed up the analysis procedure to keep up with the scanner. Currently, four servers work well for conventional scanners.

The memory of each server may be sized to hold any portion of the image data, such as an entire quadrant or a size smaller than a quadrant. If the memory of the servers can only hold a part of each quadrant, the memory is overwritten as each set of data is processed. Thus, in this example the processors need to process the image data before it is overwritten or the image data output by the inspection tool needs to slow to below the servers' processing speed. In one implementation, an array of detectors are positioned along a radius of the wafer, scanning from the outside to the inside of the wafer as the wafer rotates (or visa versa). Thus, image data is generated for annular swaths, starting at the outside and ending at the inside radius of the wafer. Alternatively, rectangular swaths of image data of the wafer are generated. No matter how the image data is collected, the server processors wait until enough data is generated to perform an inspection analysis (e.g., die-to-die). In a die-to-die example, enough image data from the wafer is collected to included two or more dies which may be compared to each.

Preferably, each server has enough memory to store a significant portion of its assigned image data. In our present example, the server memory is 8 GBytes or more so that it can store a significant portion of a specimen quadrant of image data. In an implementation where each server receives less than a quadrant (e.g., if two distributors and 8 servers are used), the memory can be smaller. That is, the memory size depends on how much the data is divided among the servers.

In an alternative procedure, an ideal die or "golden die" is stored in each server memory which is then compared to all the dies of the wafer. The golden die may be obtained in any suitable manner. For instance, the scanner may be run long enough to obtain four dies (or any other suitable number of dies) which are averaged together to form the golden die. The scanner is then backed up and rescans from the beginning. Alternatively, a backup of the scanner is not required if the golden die is generated and distributed to all the servers quickly enough to allow each server processor to analyze its image data before the server memory is overwritten (or the scanner can be slowed down initially). After a golden die is obtained, each server processor then compares all of its dies in their respective patch to the golden die. This procedure would allow the image data to be divided further ($\frac{1}{8}^{th}$ or $\frac{1}{16}^{th}$ of the wafer for one of 8 or 16 processors to processors) among more processors and processed faster. That is, two dies no longer have to be present in each processed patch for a die-to-die inspection analysis.

Embodiments of the present invention have several advantages. For example, using a high speed bus in a hierarchical two level, parallel processing system provides an efficient mechanism for determining defect information in-line during semiconductor manufacturing. That is, defects can be quickly determined and the wafer reworked before performing costly subsequent processes on the same wafer. Additionally, such a simplified two level system provides a fairly low cost solution.

Although the foregoing invention has been described in some detail for purposes of clarity of understanding, it will be apparent that certain changes and modifications may be practiced within the scope of the appended claims. Therefore, the described embodiments should be taken as illustrative and not restrictive, and the invention should not be limited to the details given herein but should be defined by the following claims and their full scope of equivalents.

What is claimed is:

1. An image processing system for analyzing images of a specimen to determine whether the specimen contains defects, the system comprising:

a plurality of processors for receiving image data from a specimen and for at least a subset of the processors each analyzing one or more selected patch(es) of such image data to determine whether the specimen has a defect;

a plurality of buses for coupling the processors together, wherein one or more the bus(es) have the following specifications: a high speed data rate of about 50 gigabits per second or more and an error rate less than about $10^{-16}$, wherein the processors are distributed between at least two boards so as to allow the system to be scaled to include additional processors and wherein the one or more bus(es) that couple processors of two different boards have the high speed data rate; and a clock module for generating a master clock for use by the processors and a pixel clock for defining pixels within the image data with respect to an angle clock of the inspection tool used for collecting the image data from the specimen, wherein the angle clock has a fixed number of pulses per a specific angle of rotation of the specimen, wherein the image data is collected from a rotating specimen and the pixel clock and synchronization signals are generated so that pixel resolution is altered according to a radial position of the specimen so as to obtain a substantially constant pixel resolution along the radius, wherein the synchronization signals indicate a relative position of the pixel clock with respect to the master clock.

2. A system as recited in claim 1, where the one or more bus(es) that have the high speed data rate are low voltage differential signal type buses.

3. A system as recited in claim 1, where the one or more bus(es) that have the high speed data rate are hyper transport type buses.

4. A system as recited in claim 1, wherein the processors are coupled together with the buses into a serial chain so that the processors sequentially receive the image data and analyze selected one or more patch(es) of such image data and wherein the processors are further operable to output one or more result signal(s) indicating whether the specimen has defects after analyzing their selected patch(es), wherein the result signal(s) of each processor are output with the image data.

5. A system as recited in claim 4, wherein the buses in the serial chain have the high speed data rate.

6. A system as recited in claim 5, wherein the buses in the serial chain are low voltage differential signal type buses.

7. A system as recited in claim 1, wherein the processors are arranged in a two level hierarchical arrangement so that one or more processors each referred to as a distributor are associated with a set of processors referred to as analyzing processors, wherein each distributor is operable to distribute a selected one or more patch(es) to each analyzing processor in its associated set for analysis of such distributed patch(es).

8. A system as recited in claim 7, wherein the distributors and their underlying analyzing processors are distributed between at least two boards so as to allow the system to be scaled to include additional distributors and their underlying analyzing processors and wherein the one or more bus(es) that couple the distributors together have the high speed data rate.

9. A system as recited in claim 7, wherein the processors include a single distributor for distributing one or more image patch(es) to each of a plurality of four associated analyzing processors, wherein each of the four analyzing processors receives a quarter of the image data from the specimen.

10. A system as recited in claim 7, wherein the processors include a first distributor for distributing one or more image patch(es) to each of a plurality of four associated analyzing processors for analysis of such distributed patch(es) and a second distributor for distributing one or more image patch (es) to each of a plurality of four associated analyzing processors for analysis of such distributed patch(es), wherein each of the eight analyzing processors receives an eighth of the image data from the specimen.

11. A system as recited in claim 10, further comprising a host for analyzing and or displaying defect data, wherein each analyzing processor is also operable to output one or more results signal(s) to the host, the result signal(s) indicating whether the specimen has a defect.

12. A system as recited in claim 1, wherein the image data corresponds to a plurality of semiconductor dies and wherein at least one or more of the processors are operable to generate a reference die based on an average of a portion of the dies of the image data and wherein one or more same or other processors are operable to compare the reference die to other dies in its image patch(es) to determine whether the specimen has a defect.

13. An image processing system for analyzing images of a specimen to determine whether the specimen contains defects, the system comprising:

a clock module for generating a master clock and a pixel clock;

a plurality of inspection signal processors for receiving different sets of optical signals obtained from an inspection tool while inspecting a specimen, wherein each inspection signal processor is operable to convert its received set of optical signals into digital image data and output such image data at a particular time slot of a the master clock sent to a next inspection signal processors if present, wherein the pixel clock is generated so as to define pixels within the image data with respect to an angle clock of the inspection tool used for collecting the image data from the specimen, wherein the angle clock has a fixed number of pulses per a specific angle of rotation of the specimen, wherein the image data is collected from a rotating specimen and the pixel clock and synchronization signals are generated so that pixel resolution is altered according to a radial position of the specimen so as to obtain a substantially constant pixel resolution along the radius, wherein the synchronization signals indicate a relative position of the pixel clock with respect to the master clock;

a distributor processor for receiving the image data from the plurality of inspection signal processors and for dividing the image data into a plurality of image patches; and a plurality of analyzing processors associated with the distributor, wherein the distributor is further operable to distribute selected image patches to selected analyzing processors for parallel processing to determine whether the specimen has a defect, wherein the inspection signal processors are distributed among a plurality of boards so that there is at least one inspection signal processor per board and the signal processors are serially coupled together by a high speed bus having the following specifications: a data rate of about 50 gigabits per second or more and an error rate less than about $10^{-16}$.

14. A system as recited in claim 13, wherein the distributor receives the image data from a last one of the inspection signal processors after all of the inspection signal processors have contributed to the image data.

15. A system as recited in claim 14, wherein there are 12 inspection signal processors and eight analyzing processors.

16. A system as recited in claim 15, wherein there are two inspection signal processors per board, the distributor and associated analyzing processors are on a single board, and the inspection signal processors and the distributor are serially coupled together by a high speed bus having the following specifications: a data rate of about 50 gigabits per second or more and an error rate less than about $10^{-16}$.

17. A system as recited in claim 16, wherein the high speed bus is a low voltage differential signal type bus.

18. A system as recited in claim 13, wherein the analyzing processors are each further operable to send a signal to the inspection tool indicating that the inspection tool needs to decrease its image data output speed when the speed is greater than the each analyzing processor can process its image patch(es).

19. A system as recited in claim 13, wherein the optical signals are received in the form of annular swaths of the specimen.

20. A system as recited in claim 13, wherein the optical signals are received in the form of rectangular swaths of the specimen.

* * * * *

UNITED STATES PATENT AND TRADEMARK OFFICE
CERTIFICATE OF CORRECTION

PATENT NO. : 7,215,808 B2  Page 1 of 1
APPLICATION NO. : 10/860617
DATED : May 8, 2007
INVENTOR(S) : Lawrence R. Miller It is certified that error appears in the above-identified patent and that said Letters Patent is hereby corrected as shown below:

On the title page item (54), and col. 1, line 1, change "THROUGHOUT" to --THROUGHPUT--.

Signed and Sealed this

Third Day of June, 2008

JON W. DUDAS
*Director of the United States Patent and Trademark Office*